United States Patent

Pigneul et al.

[11] Patent Number: 5,118,376
[45] Date of Patent: Jun. 2, 1992

[54] PROCEDURE OF INCORPORATION OF POWDERY PRODUCTS WITHIN A FIBER PADDING AND DEVICE FOR ITS OPERATION

[75] Inventors: Raymond Pigneul, Durrenentzen; Rémy Ruppel, Horbourg, both of France

[73] Assignee: Kaysersberg, SA, Kaysersberg, France

[21] Appl. No.: 31,557

[22] PCT Filed: Jun. 18, 1986

[86] PCT No.: PCT/FR86/00208
§ 371 Date: Feb. 24, 1987
§ 102(e) Date: Feb. 24, 1987

[87] PCT Pub. No.: WO87/00057
PCT Pub. Date: Jan. 15, 1987

[30] Foreign Application Priority Data

Jun. 24, 1985 [FR] France ............. 85 09611

[51] Int. Cl.⁵ .................................. B32B 31/20
[52] U.S. Cl. ........................ 156/219; 156/276; 156/292
[58] Field of Search .......... 156/62.2, 62.8, 276, 156/219, 292; 604/365, 368, 380

[56] References Cited

U.S. PATENT DOCUMENTS

| 3,884,741 | 5/1975 | Sexstone | 156/276 |
| 4,055,180 | 10/1977 | Karami | 604/368 |
| 4,260,443 | 4/1981 | Lindsay | 604/368 |
| 4,333,462 | 6/1982 | Holtman | 604/368 |
| 4,333,463 | 6/1982 | Holtman | 604/368 |
| 4,662,876 | 5/1987 | Wiegner | 604/380 |

FOREIGN PATENT DOCUMENTS 1315431  5/1973  United Kingdom ............ 604/368

Primary Examiner—Jenna L. Davis
Attorney, Agent, or Firm—Breiner & Breiner

[57] ABSTRACT

The procedure consists in compressing locally the fiber padding by means of a specifically profile tool, and in placing the powdery product in the impression left by the tool. According to an additional characteristic of the procedure, a compression force is then applied on the product in order to set it in the fibrous mass.

A device for the operation of the procedure is made of two cylinders (20, 30) connected by a belt (40). The teeth of the first cylinder (23) fashion the impressions; the perforations (41) of the belt permit the localization of the powder in the impressions, and the teeth of the second cylinder (33) enable its setting.

The procedure concerns especially the incorporation of superabsorbent material in the fiber padding of disposable hygiene articles.

5 Claims, 2 Drawing Sheets

PROCEDURE OF INCORPORATION OF POWDERY PRODUCTS WITHIN A FIBER PADDING AND DEVICE FOR ITS OPERATION

The invention concerns the field of disposable articles, intended for the absorption of fluids and consisting of an absorbent padding made of fibers, and relates to a procedure and device permitting the incorporation of powdery products, especially superabsorbent, within the padding.

In order to reduce the volume of the padding of articles such as baby diapers, pads for incontinents, sanitary napkins, panty liners etc. . . . or to increase their absorption ability, it is attempted to incorporate to the padding superabsorbent products, usually called additives with improved water retention, hydroretainers. These products are usually presented in the form of granules, particles, powders: they are compounds which swell in the presence of fluids but are insoluble: they cause the formation of a gel, the volume of which may be several dozens of times the volume of the dry product. The most well known products are alginates, reticular carboxymethylcelluloses, grafted starches, synthetic derivatives of acrylamide or acrylate types.

Since they are materials of a different nature: granules/fibers, their mixture does not remain homogeneous in time. This phenomenon is the more marked as the articles of which they are the components undergo numerous manipulations and deformations during transportation and during usage. As a matter of fact, a migration of the powder towards areas of the padding where it becomes ineffective, is noticed.

The fixation of superabsorbent products on their support was the subject of many studies. They may be fixed by moistening insuring successively their partial gelification, their deposit, then their drying on the support. This technique has the disadvantage of modifying the surface condition of the particles and therefore their efficacy. In addition, the drying stage required by the procedure increases the manufacturing cost of these articles.

It is also possible to insure fixation with binding agents, as described in U.S. Pat. No. 3,903,889 and FR patent 2402474 where the product is maintained by a layer of adhesive material. However, it appeared that the binding agent prevented the expansion of the product and reduced the active surface of the granule.

In the U.S. Pat. Nos. 4,055,180 or 4,381,783 the superabsorbent is encased between support sheets bound together in order to form pockets. These sheets may be impermeable, perforated with apertures to allow the passing of fluids, or they may be permeable. Thus, the migration of particles during manipulation of the article is avoided. But the confinement of the gel is insured: rising towards the material covering the article, on the skin side, is avoided and any risk of contact between gel and the patient's skin is eliminated. However, since the sides of these pockets are not stretchable, the action of the product is limited. In addition, these additional sheets form an obstacle to the passage of fluids and prevent a rapid absorption.

We have also tried to incorporate particles directly into the absorbent padding. The U.S. Pat. No. 3,888,257 described a procedure of incorporation using compressed air jets for the penetration of the particles, previously placed on the surface within the fiber padding. This procedure is a delicate operation since the air jets have a tendency to destabilize the padding which loses its homogeneous characteristic.

The FR patent 2446357 describes a procedure where the powdery product is placed between the padding and a sheet of fibers, bound together along lines or points, in order to define confinement spaces. The binding is performed by simple cold die-casting by means of cylinders engraved with square patterns, or by hot calendering when the fibers are easily melted. The advantage of this solution is it may be carried out quite inexpensively: it insures a good adherence of the particles between the sheets and takes advantage of the elasticity of the fibers to allow the expansion of the gel. However, in this solution, the superabsorbent product remains on the surface of the padding and forms a continuous deposit.

After a first flow of fluid, the gel forms a uniform barrier limiting the subsequent diffusion of fluid towards the deeper layer of the padding which could be able to absorb it. Thus, in baby diapers for instance, even by anticipating a capacity of absorption sufficient enough for a normal use, leaks occur because the fluids are not sufficiently and rapidly absorbed, because of gel formation. To solve this problem, the invention intends to fragment the powder deposit in order to delay the formation of a continuous barrier and permit the passage of fluids in the lower layers of the padding and settle the powder at the bottom of the padding so that the fibers, diffusing the fluids towards the absorbent product, are mainly interposed between the source of fluid and the superabsorbent product.

The procedure of incorporation of powdery products, especially superabsorbent products, to a fiber padding, such as cellulose foam, for a disposable article is characterized in that it consists of a local compression of the padding by means of a specifically profiled tool and of depositing the powdery product inside the impression made with the tool.

The impression will preferably form an alveole of which the section will essentially depend on the application: it may be circular, oblong, square or rectangular.

The procedure concerns particularly the manufacture of disposable articles: baby diapers, pads for incontinents, sanitary napkins, panty liners, etc. . . . of which the fiber padding in made of cellulose foam obtained by dry extraction of the fibers of paperpaste sheets. But it also concerns paddings containing other types of fibers, bound or unbound.

The powdery products here, are essentially superabsorbent but other additives may be incorporated in the same fashion. The superabsorbent products which could be used are found commercially in a powdery form: particles, granules. This form offers an optimal surface/volume ratio permitting a maximum absorption of the molecules of fluid.

According to another characteristic of the invention, after depositing the product in the alveole or the impression, a compression is applied towards the bottom of the alveole in order to set it, at least partially within the mass of fibers.

According to another characteristic of the invention, the product is distributed in many alveoles placed in the padding according to a well-defined pattern.

With this procedure, a product is obtained and the distribution of the powder in the mass in order to optimize its action, is perfectly and easily mastered.

From U.S. Pat. No. 4,435,178 we already know of a hygiene article with an absorbing padding which includes two superposed sheets. In the skin side sheet, are distributed cylindrical alveoles which are open towards the side receiving the fluid. The function of these alveoles is to canalize the fluids towards the inside of the padding and they are kept open by enduction of the walls with consolidation product which may accessorily be a superabsorbent. The design of such an article, concerning the enduction of the alveoles, does not seem to be economically feasible as a simple procedure permitting a high production rhythm. In addition, the continuous form, undivided, of the superabsorbent, makes its efficacy doutful.

According to another aspect of the invention, the padding may then be covered with a fibrous sheet with interposition of a layer of a binding agent, in order to improve the confinement and limit the rising of the gel. This sheet of fibers is interestingly made of paper cellulose fibers bound with latex according to the technique described for instance in FR patent 2418829.

The following description, in reference to the enclosed drawings, relates to the mode of realization, as a non limiting example, of a device for implementing the procedure:

Figure 1:
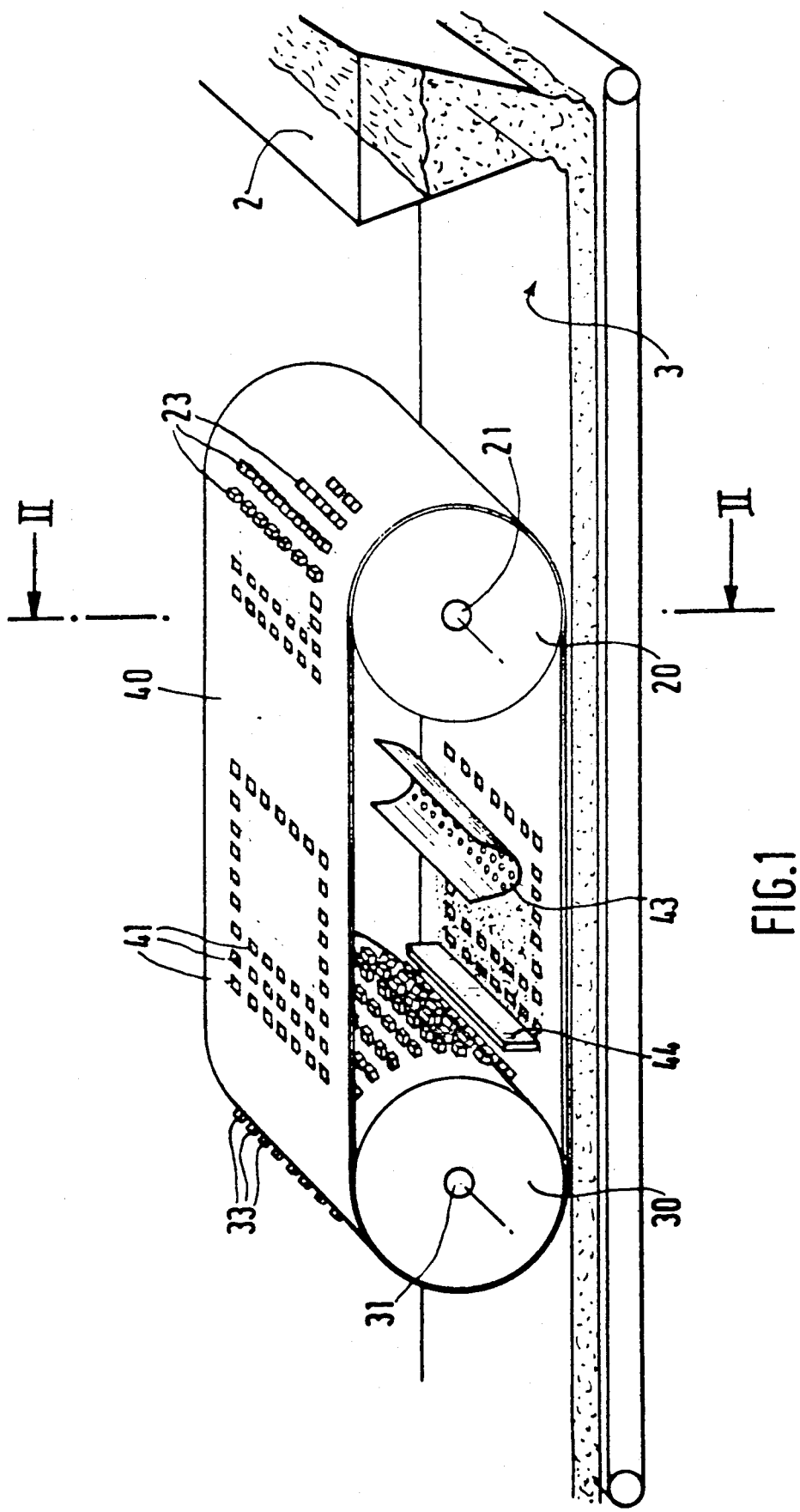
FIG. 1 represents, in isometric perspective, the device according to the invention placed on a padding of fibers.
Figure 2:
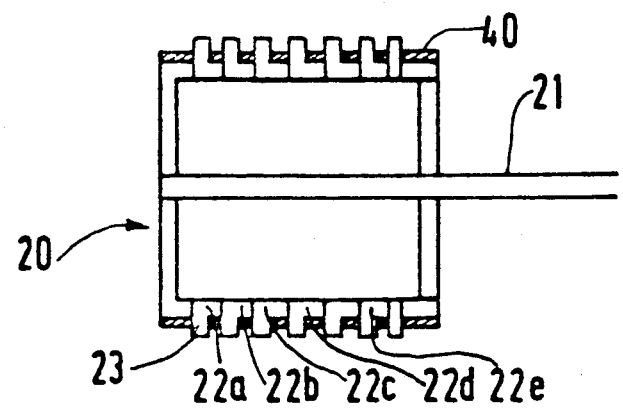
FIG. 2 is a section according to II—II on FIG. 1.

On FIG. 1, a device of insertion of the superabsorbent is schematically represented, according to the invention, integrated in a line of continuous manufacture of disposable hygiene articles; only the proximal part in relation with the formation of the cellulose foam padding is represented. This foam, after the operation of dry extraction of the fibers of paperpaste sheets, is introduced in a funnel 2 through which it is distributed on a conveyor belt to form a padding 3 of specific weight and size.

The device according to the invention is made of two identical cylinders 20, 30 with a rotary mount around two parallel axles 21, 31 and connected with an endless belt 40 approximately of the same width as the cylinders. The device is suspended above the padding, with the axles 21, 31 placed transversally in relation to the movement of the padding, and the inferior portion of the belt placed flat on the padding without exerting any compression force.

The belt and the cylinders are measured and driven in a synchronous fashion, so that the belt moves about with the padding at the same speed, without sliding.

Cylinder 20 presents crowns 22a, 22b, 22c . . . and cylinder 30 presents crowns 32a, 32b, 32c, not shown . . . identical at least two by two from one cylinder to the other. The crowns of one cylinder are parallel to each other and placed transversally in relation to the axle of the cylinder. Each crown has a specific number of teeth 23, 33 distributed in one or several sections according to the application, two under the circumstances. Each crown 22a, 22b . . . of the first cylinder is identical and placed in the same plane as the corresponding crown 32a, 32b . . . of the second cylinder.

The belt 40 presents perforations 41, arranged into blocks, corresponding, in number, size and arrangement to the teeth of a segment of cylinder covered with teeth. This relative disposition between belt and cylinders is to permit, according to the first function of the belt, a perfect synchronism between the cylinders. The teeth of each crown from each cylinder engage in the same perforations as the corresponding teeth of the corresponding crown of the other cylinder.

The teeth protrude outside the external surface of the belt. Their height is selected in function of the thickness of the padding. The teeth must be able to penetrate the padding in order to compress it at a specific depth without going through it, for all that. The heights are preferably equal from one cylinder to the other.

Between the two cylinders and the loop formed by the belt, a dispenser 43 of superabsorbent powder is installed. This dispenser may be made, as it is known, of a vibrating groove insuring the deposit of powder on a strip of specific width equal to the width of the blocks formed by the perforations of the belt. The powder is therefore deposited partly in the perforations, partly on the internal surface of the belt between perforations. A scraper 44 placed distal to the dispenser in relation to the direction of translation of the belt, pushes back the residual powder into the apertures of the belt. A device for a possible recovery, not represented here, eliminates the excess of powder that has not been pushed back into the apertures.

This device functions as follows:

After being formed, the padding moves about in translation on the conveyor belt to the first cylinder 20 of the device, where the teeth 23 of a segment imprint a series of rows of alveoles in the mass. Distal to this cylinder, the teeth are withdrawn leaving their impression. To the right of the vibrating dispenser, part of the powder deposited by the groove 43 on the belt, passes directly through the perforations 41 in the alveoles, and another part of the powder is pushed back towards the alveoles by the scraper 44. When the padding reaches the level of the second cylinder, the teeth 33 of this cylinder penetrate in the alveoles formes by the first cylinder, through apertures 41 of the belt and they push the particles of superabsorbent product towards the bottom. After rotation of the cylinder the teeth withdraw from the alveoles and the padding continues its translation incrusted with the particles of superabsorbent deposited in specific quantity at the bottom of a specific number of alveoles.

To this padding is then associated a sheet of fibers bound with latex according to the procedure of FR patent 2418829. This sheet is deposited on the padding after pulverization of threads of glue easily melted; the complex thus formed is then encased between a permeable, non woven veil on the side of the article coming in contact with the skin of the user and an impermeable sheet, in polyethylen for instance, on the outside. Finally, the padding is sealed and cut into individual articles, the division being made in the zone without alveoles between the two blocks.

Figure 3:
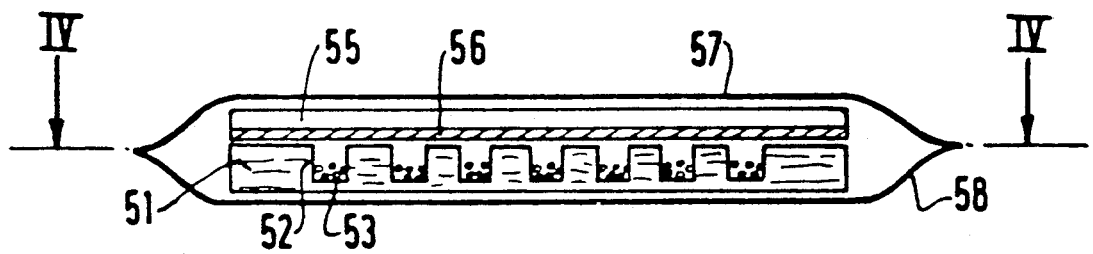
FIG. 3 is a cross-section, at a different scale, of a disposable hygiene article made up of superabsorbent particles incorporated in the padding of fibers according to the procedure of the invention.
Figure 4:
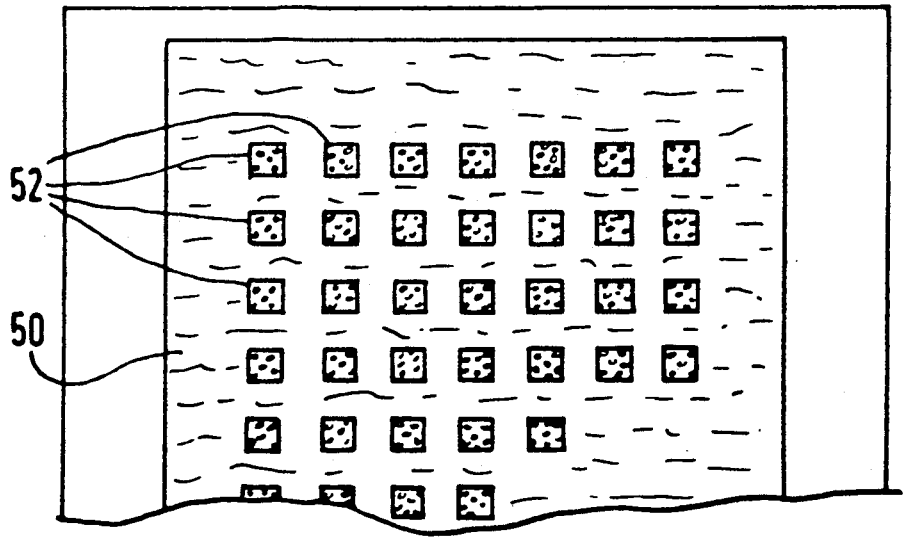
FIG. 4 is a section view according to IV—IV of FIG. 3.

FIG. 3 and 4 represent schematically the formation of such an article of which the characteristics, given as an example, may be as follows:

The rectangular padding 51 is made of cellulose foam weighing 300 g/m2, its longitudinal and transversal dimensions are 430 mm and 145 mm, the mean thickness is 3.5 mm.

The padding presents 24 rows of 8 alveoles 52, cylindrical, of 10 mm of diameter and 1.7 mm of depth. The powdery product is localized at the bottom of the alveoles. in the proportion of 4.5 g per pad, and it is, at least partially, encrusted in the cellulose foam. A sheet 55 of paper fibers bound with a latex, weighing 65 g/m2, is associated to the padding through a layer 56 of adhesive material deposited by enduction or by the so called technique of pulverization of easily heat-melted glue. The ensemble is encased between a permeable non-woven veil 57 and a permeable sheet 58 of polyethylen, joined edge to edge.

With this localization of the superabsorbent in distinct areas, diffusion zones facilitating the absorption of fluids are arranged.

On the other hand, this process permits to delay the formation of a continuous layer of gel.

We claim:

1. Method for the incorporation of a fluid-absorbing powdery product into a fiber padding for disposable articles comprising compressing said fiber padding so as to form a plurality of impressions arranged according to a predetermined, defined pattern; depositing a fluid-absorbing powdery product into said impressions, and thereafter compressing said powdery product into the bottom of said impressions to thereby segregate said powdery product in said impressions.

2. The method according to claim 1 wherein said powdery product is a superabsorbent material.

3. The method according to claim 2 wherein the fiber padding comprises cellulosic foam.

4. The method according to one of claims 1, 2 or 3 wherein a fibrous sheet material is applied to one surface of said fiber padding.

5. The method according to claim 4 wherein said sheet material is bonded to said fiber padding with an adhesive substance.

* * * * *